(12) United States Patent
Sambusseti et al.

(10) Patent No.: US 10,092,383 B2
(45) Date of Patent: Oct. 9, 2018

(54) ARTIFICIAL SPHINCTER

(71) Applicants: Antonio Sambusseti, Cremona (IT); Gianni Cancarini, Brescia (IT)

(72) Inventors: Antonio Sambusseti, Cremona (IT); Gianni Cancarini, Brescia (IT)

( * ) Notice: Subject to any disclaimer, the term of this patent is extended or adjusted under 35 U.S.C. 154(b) by 79 days.

(21) Appl. No.: 15/320,525

(22) PCT Filed: Jun. 8, 2015

(86) PCT No.: PCT/IB2015/054320
§ 371 (c)(1),
(2) Date: Dec. 20, 2016

(87) PCT Pub. No.: WO2015/198179
PCT Pub. Date: Dec. 30, 2015

(65) Prior Publication Data
US 2017/0143462 A1    May 25, 2017

(30) Foreign Application Priority Data

Jun. 27, 2014  (IT) .............................. MI2014A1175

(51) Int. Cl.
*A61F 2/02*  (2006.01)
*A61F 2/00*  (2006.01)

(52) U.S. Cl.
CPC ........ *A61F 2/004* (2013.01); *A61F 2220/005* (2013.01); *A61F 2220/0091* (2013.01); *A61F 2230/0013* (2013.01); *A61F 2230/0067* (2013.01); *A61F 2230/0069* (2013.01); *A61F 2250/0003* (2013.01)

(58) Field of Classification Search
CPC ...... A61F 2/004; A61F 2/0013; A61F 2/0027; A61F 2/0004; A61F 2/0031
USPC ...................................................... 600/29–32
See application file for complete search history.

(56) References Cited

U.S. PATENT DOCUMENTS

| | | | |
|---|---|---|---|
| 4,553,271 A * | 11/1985 | Baker | A61F 2/0036 600/30 |
| 4,587,955 A | 5/1986 | Gengler | |
| 2010/0312052 A1 | 12/2010 | Morningstar | |
| 2012/0123195 A1 | 5/2012 | Woodruff et al. | |
| 2013/0079588 A1 | 3/2013 | Crabtree et al. | |
| 2013/0190557 A1 | 7/2013 | Hoover et al. | |

OTHER PUBLICATIONS

International Search Report and Written Opinion dated Sep. 24, 2015 for PCT/IB2015/054320 to Antonio Sambusseti et al. filed Jun. 8, 2015.

* cited by examiner

*Primary Examiner* — John Lacyk
(74) *Attorney, Agent, or Firm* — Vorys, Sater, Seymour and Pease LLP

(57) ABSTRACT

An artificial sphincter includes at least two elements associated with each other and hollow for containing a pressurized fluid; the elements being adapted to be arranged on the sides of the urethra of a patient and have a substantially semi-conical shape; each element has a respective contact surface with the urethra of substantially semi-cylindrical shape.

7 Claims, 2 Drawing Sheets

ARTIFICIAL SPHINCTER

CROSS-REFERENCE TO RELATED APPLICATIONS

This is a § 371 National Stage Application of International Application No. PCT/IB2015/054320 filed on Jun. 8, 2015, claiming the priority of Italian Patent Application No. MI2014A001175 filed on Jun. 27, 2014.

FIELD OF THE INVENTION

The object of the present invention is an artificial sphincter.

In particular, the present invention can be applied in the regulation of a urine flow in the urological apparatus of a patient.

BACKGROUND OF THE INVENTION

According to the prior art, artificial sphincters comprise two hollow balls arranged around the urethra of the patient, directly downstream of the bladder.

The balls are filled with physiological solution so as to exert a pressure on the urethra in a manner such to ensure the seal thereof, preventing the outflow of urine, up to a specific urine pressure. When the pressure exerted by the urine on the urethra exceeds the pressure exerted by the sphincter on the urethra, the urine flows out.

The pressure of the physiological solution within the balls can be regulated by increasing or decreasing the quantity of liquid introduced through two afferent ducts accessible from outside the patient.

Examples of devices which can be used for the treatment of also sphincter pathologies can be seen in U.S. Pat. No. 4,587,955, U.S. 2010/312052 and U.S. 2012/123195.

U.S. Pat. No. 4,587,955 discloses a mechanical latch for securing an artificial sphincter device within the body and, more in particular a mechanical latch which secures a belt about an inflatable cuff portion of an artificial sphincter; disadvantageously, this solution has not produced optimal results. Indeed, the two balls are unable to remain in the assigned position for a long period. In such a manner, being moved, they determine a non-ideal contact with the patient's urethra and do not ensure the desired seal.

Alternatively, in U.S. 2010/312052 it is disclosed an anatomical augmentation device which is configured to augment a tubular member of a human body; according to said solution a ring is used that can be wound around the urethra, it is also fillable with physiological solution. Also in this case, the pressure inside the ring can be regulated by adjusting, from the outside, the quantity of liquid introduced into the ring itself.

Also this solution, nevertheless, is not at all satisfactory. Indeed the ring progressively tends to be sclerosed, losing the necessary seal and, with this, its functionality.

U.S. 2012/123195 discloses a gastric band which is also suitable to be used for the treatment of fecal incontinence or urinary incontinence.

SUMMARY OF THE INVENTION

In this context, the technical task underlying the present invention is to propose an artificial sphincter that overcomes the drawbacks of the abovementioned prior art.

In particular, an objective of the present invention is to provide an artificial sphincter that is effective and reliable over time.

The specified technical task and specified object are substantially achieved by an artificial sphincter comprising the technical characteristics set forth in one or more of the enclosed claims.

BRIEF DESCRIPTION OF THE DRAWINGS

Further characteristics and advantages of the present invention will be clearer from the exemplifying and hence non-limiting description of a preferred but not exclusive embodiment of an artificial sphincter, as illustrated in the enclosed drawings, in which.

Figure 1:
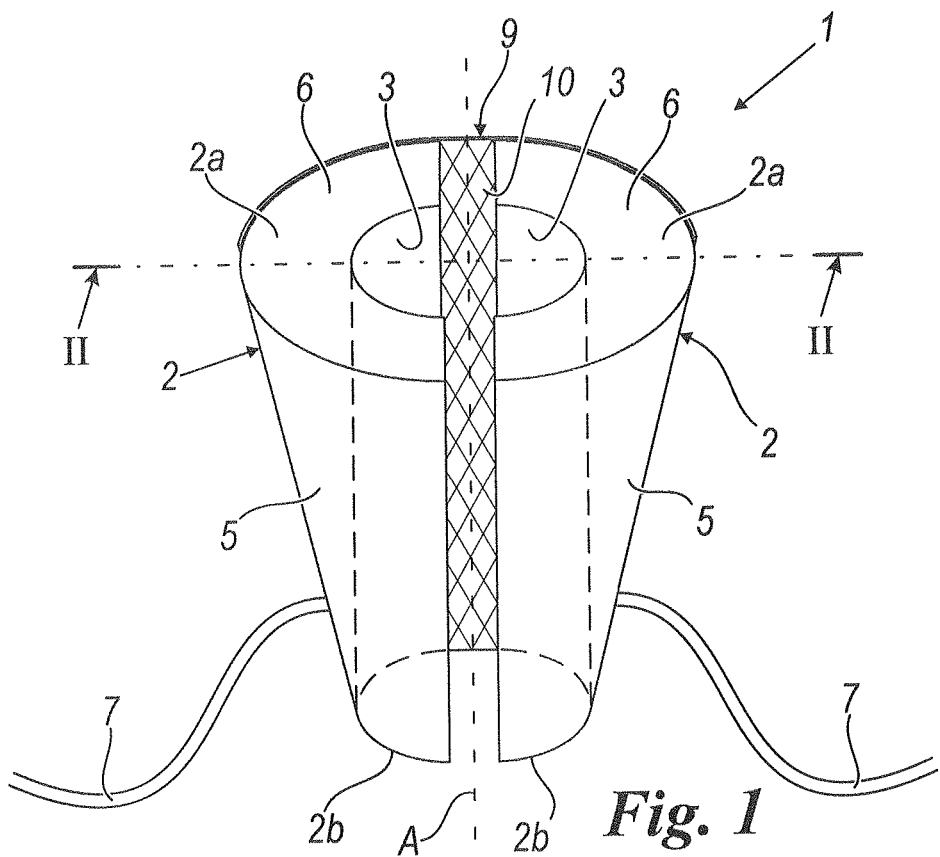
FIG. 1 is a perspective view of an artificial sphincter in accordance with the present invention.
Figure 2:
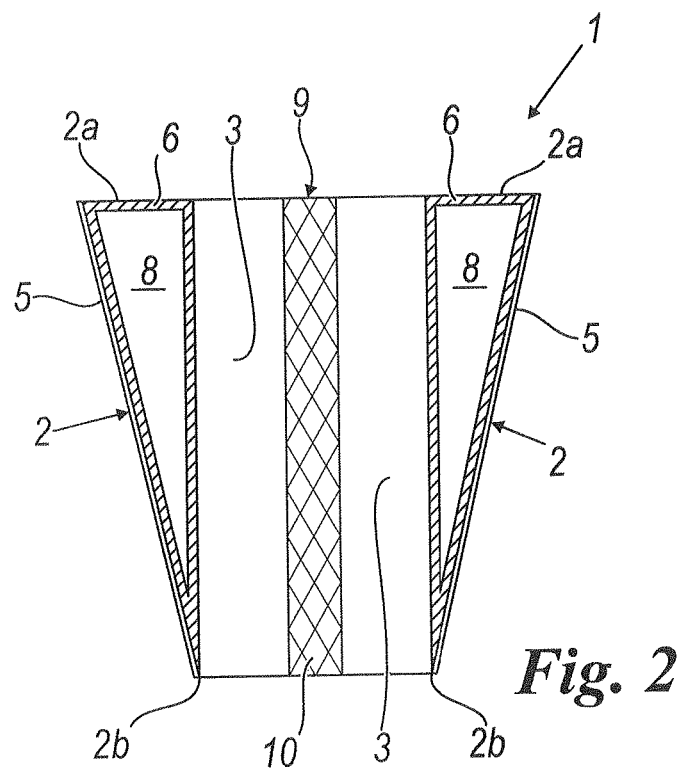
FIG. 2 is a side sectional view of the artificial sphincter of FIG. 1 along the section plane II-II.
Figure 3:
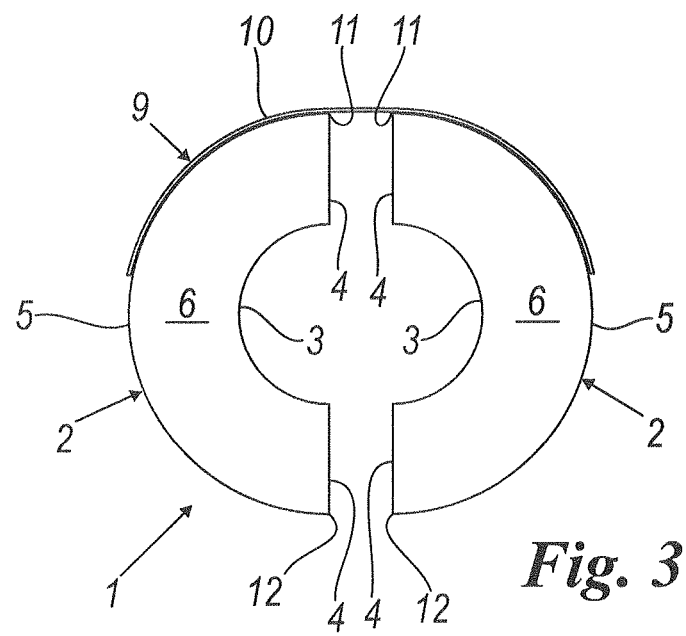
FIG. 3 is a plan view of the artificial sphincter of FIG. 1; and the view 4 is a perspective view of the artificial sphincter of FIG. 1 according to a different angle.
Figure 4:
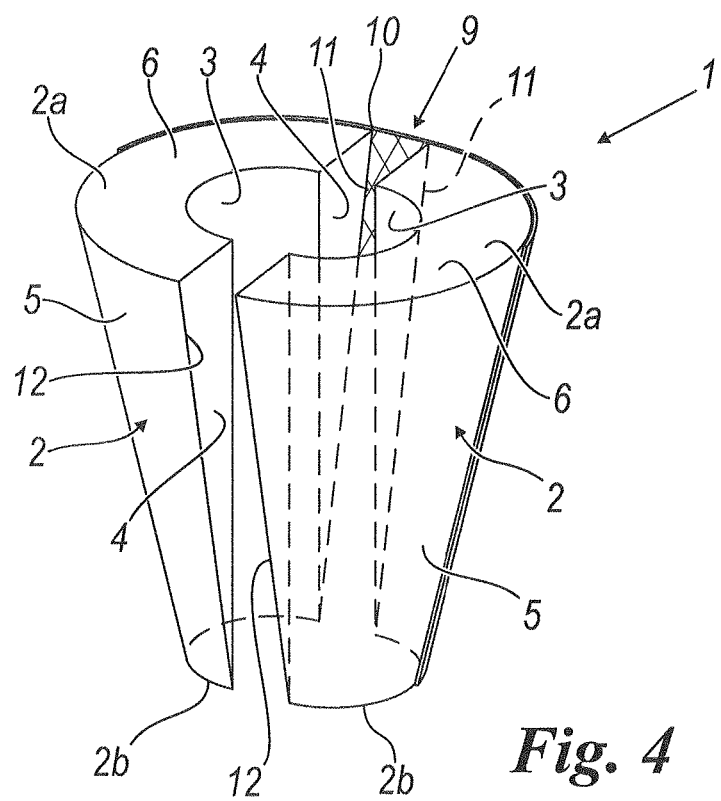

With reference to the enclosed figures, reference number 1 overall indicates an artificial sphincter in accordance with the present invention.

DETAILED DESCRIPTION OF THE PREFERRED EMBODIMENTS

The sphincter 1 comprises two elements 2 that are equivalent, mutually facing and connected to each other. The elements 2 have elongated form along an extension axis "A".

The elements 2 are internally hollow in order to allow containing a pressurized fluid. By way of example, the fluid is physiological solution.

The elements 2 are arranged along the urethra and, more precisely, on opposite sides of the same.

More in detail, the elements 2 connected with each other, during use, are arranged with a respective first end 2a in a position proximal to the bladder and with a respective second end 2b in a distal position.

Each element 2 has a respective contact surface 3 of a substantially semi-cylindrical shape for coming into contact with the opposite sides of the urethra.

Advantageously, in such a manner, the contact between the elements 2 and the urethra occurs on a wide surface. The action of the elements 2 is therefore improved and the coupling with the urethra clearly becomes stable.

In detail, the elements 2 exert, on the urethra of the patient through the contact surfaces 3, a pressure decreasing from the first 2a to the second end 2b.

In other words, the elements 2 exert a greater pressure in proximity to the bladder, where the pressure exerted by the urine is greater, and exert a lower pressure moving away from the bladder, concordantly with the decreasing progression of the pressure from the urine along the urethra.

This allows exerting an optimal pressure along the length of the urethra in contact with the elements 2.

In accordance with that stated above, each element 2 has a substantially semi-conical shape.

In detail, each element 2 has a flat surface 4 and a semi-conical surface 5, facing the flat surface 4. The contact surface 3 is obtained along the entire length of each flat surface 4 along the axis "A". In fact, each flat surface 5 is divided into two portions by the contact surface 3.

A base surface 6, which is also flat, completes the elements 2.

In such a manner, each element 2 has a cross section at the longitudinal extension axis "A" with area decreasing from the first 2a to the second end 2b.

The artificial sphincter 1 further comprises two ducts 7 associated with a respective element 2.

As stated, the elements 2 are hollow and at their interior define a cavity 8 for containing a pressurized fluid which, preferably, is a physiological solution.

The ducts 7 are in fluid communication with the respective cavities 8 so as to be able to introduce and extract the physiological solution therein and to regulate, in such a manner, the pressure that the fluid exerts.

During use, when the artificial sphincter 1 is installed in the patient, the ends of the ducts 7 not connected to the elements 2 are outside the patient himself/herself in a manner such that the adjustment of the pressure of the physiological solution can also be subsequently carried out.

The elements 2 are made of biocompatible material. Preferably, the elements 2 are made of silicone. Alternatively, the elements 2 can be made of polysulphone, polyester or polyurethane. Such materials allow the elements 2 to adhere to the adjacent biological tissues in order to allow an effective anchoring of the artificial sphincter 1.

In addition, each contact surface 3 is covered with a layer of pyrolytic turbostratic carbon. This allows the prevention of such contact surfaces 3 from attaching to the urethra of the patient in order to prevent deformations or stenosis.

The thickness of such layer of pyrolytic turbostratic carbon comprises between 0.1 mm and 0.3 mm and is preferably substantially equal to 0.2 mm.

The artificial sphincter 1 further comprises a connection member 9 arranged between the elements 2 in order to connect them.

This allows the prevention of excessive relative movements between the elements 2.

In the preferred embodiment, the connection member 9 comprises a strip 10 of biocompatible fabric fixed on the semi-conical surfaces 5 of the elements 2.

Preferably, the fixing between the strip 10 of fabric and the semi-conical surfaces 5 occurs by means of gluing. In other words, the strip 10 has a first end fixed to one of the elements 2 and a second end fixed to the other element 2.

Advantageously, the connection member 9 is only active at the first facing edges 11 of the elements 2.

The first edges 11 are those defined between the semi-conical surface 5 and the flat surface 4 facing each other and arranged on one side of the artificial sphincter 1. Naturally, also second facing edges 11 are defined, and these are those defined between the semi-conical surface 5 and flat surface 4 facing each other and arranged on the opposite side of the artificial sphincter 1.

The strip 10 only passes in proximity to the first edges 11. In this manner, a substantially hinge-like connection is defined between the elements 2. The translation of such elements 2 is limited to the length of strip 10 not fixed to the semi-conical surfaces 5, and such elements 2 can rotate with respect to each other.

In such a manner, the relative position between the elements 2 is substantially ensured, while at the same time a rigidity is also prevented that could cause damage to the tissues of the patient or failures of the sphincter 1.

Alternatively, the connection member 9 comprises two or more strips of biocompatible fabric fixed to the elements 2 and all arranged on the same side of the artificial sphincter 1.

The invention thus described attains the proposed object. Indeed, the artificial sphincter in accordance with the present invention allows the maintaining, for a long time, of both the correct position with respect to the urethra and its functionality.

Indeed, the presence of the counter-shaped contact surfaces of the urethra allows the elements to assume a stable position over time.

Also the substantially semi-conical shape of the elements that form the sphincter allows an easy and stable anchoring in the pelvis of the patient.

The invention claimed is:

1. An artificial sphincter comprising at least two elements connected to each other and hollow for containing a pressurized fluid;
   said elements being adapted to be arranged on the sides of the urethra of a patient;
   each element having a respective contact surface with the urethra of substantially semi-cylindrical shape;
   wherein each element has a semi-conical surface opposite the contact surface,
   wherein said elements exert a decreasing pressure on the urethra from a first end arranged, during use, in a position proximal to the bladder of the patient, to a second end arranged, during use, in a position distal from the bladder of the patient,
   wherein each element has a cross section having area decreasing from a first end arranged, during use, in a position proximal to the bladder of the patient, to a second end arranged, during use, in a position distal from the bladder of the patient.

2. The sphincter according to claim 1, comprising an operative connection member arranged between the elements.

3. The sphincter according to claim 2, wherein said connection member comprises a strip of biocompatible fabric fixed on the semi-conical surfaces of the elements.

4. The sphincter according to claim 2, wherein the elements have first facing edges, wherein said connection member is only active at the first facing edges of the elements, wherein said connection member defines a hinge-like connection between the elements at the first facing edges.

5. The sphincter according to claim 1, wherein said elements are made of silicone.

6. The sphincter according to claim 1, wherein each contact surface is covered with a layer of pyrolytic turbostratic carbon.

7. The sphincter according to claim 1, comprising ducts connected to each element for inserting and/or removing fluid from said elements themselves.

* * * * *